US012496219B2

(12) United States Patent
Tanabe

(10) Patent No.: US 12,496,219 B2
(45) Date of Patent: Dec. 16, 2025

(54) GLAUCOMA DRAINAGE TUBE

(71) Applicant: Hirotaka Tanabe, Nagoya (JP)

(72) Inventor: Hirotaka Tanabe, Nagoya (JP)

( * ) Notice: Subject to any disclaimer, the term of this patent is extended or adjusted under 35 U.S.C. 154(b) by 953 days.

(21) Appl. No.: 17/690,234

(22) Filed: Mar. 9, 2022

(65) Prior Publication Data

US 2023/0049991 A1 Feb. 16, 2023

(30) Foreign Application Priority Data

Aug. 16, 2021 (JP) ................................ 2021-132238

(51) Int. Cl.
*A61F 9/007* (2006.01)
*A61M 1/00* (2006.01)

(52) U.S. Cl.
CPC ........... *A61F 9/00736* (2013.01); *A61M 1/84* (2021.05)

(58) Field of Classification Search
CPC ................. A61F 9/00736; A61M 1/84; A61M 2210/0612
See application file for complete search history.

(56) References Cited

U.S. PATENT DOCUMENTS

| | | | | |
|---|---|---|---|---|
| 3,788,327 | A | 1/1974 | Donowitz et al. | |
| 5,041,081 | A * | 8/1991 | Odrich | A61F 9/00781 604/9 |
| 7,431,709 | B2 | 10/2008 | Pinchuk et al. | |

OTHER PUBLICATIONS

Screen captures and transcript from YouTube video clip entitled "The Surprising Link Between Our Heartbeat and Our Eye Health", 17 pages, uploaded on Jul. 13, 2021 by user / channel "Animate Your Science TV".[retrieved on Apr. 8, 2022]. Retrieved from the Internet <URL: https://www.youtube.com/watch?v=srLSBEmm4Ew>.

Tanabe, H. et al., "Heart rhythm-synchronized fibrin flap in a glaucoma tube shunt," Medicine, vol. 100, No. 27, Jul. 2021, Wolters Kluwer Health, Inc., 4 pages.

* cited by examiner

*Primary Examiner* — Deanna K Hall
(74) *Attorney, Agent, or Firm* — Withrow + Terranova, PLLC; Vincent K. Gustafson

(57) ABSTRACT

A glaucoma drainage tube is provided. The glaucoma drainage tube is a glaucoma drainage tube for draining aqueous humor, and includes a canal through which the aqueous humor flows, and a displacement member that is arranged at an inlet of the canal and is displaced so as to reciprocate in response to a flow of the aqueous humor flowing therein.

7 Claims, 1 Drawing Sheet

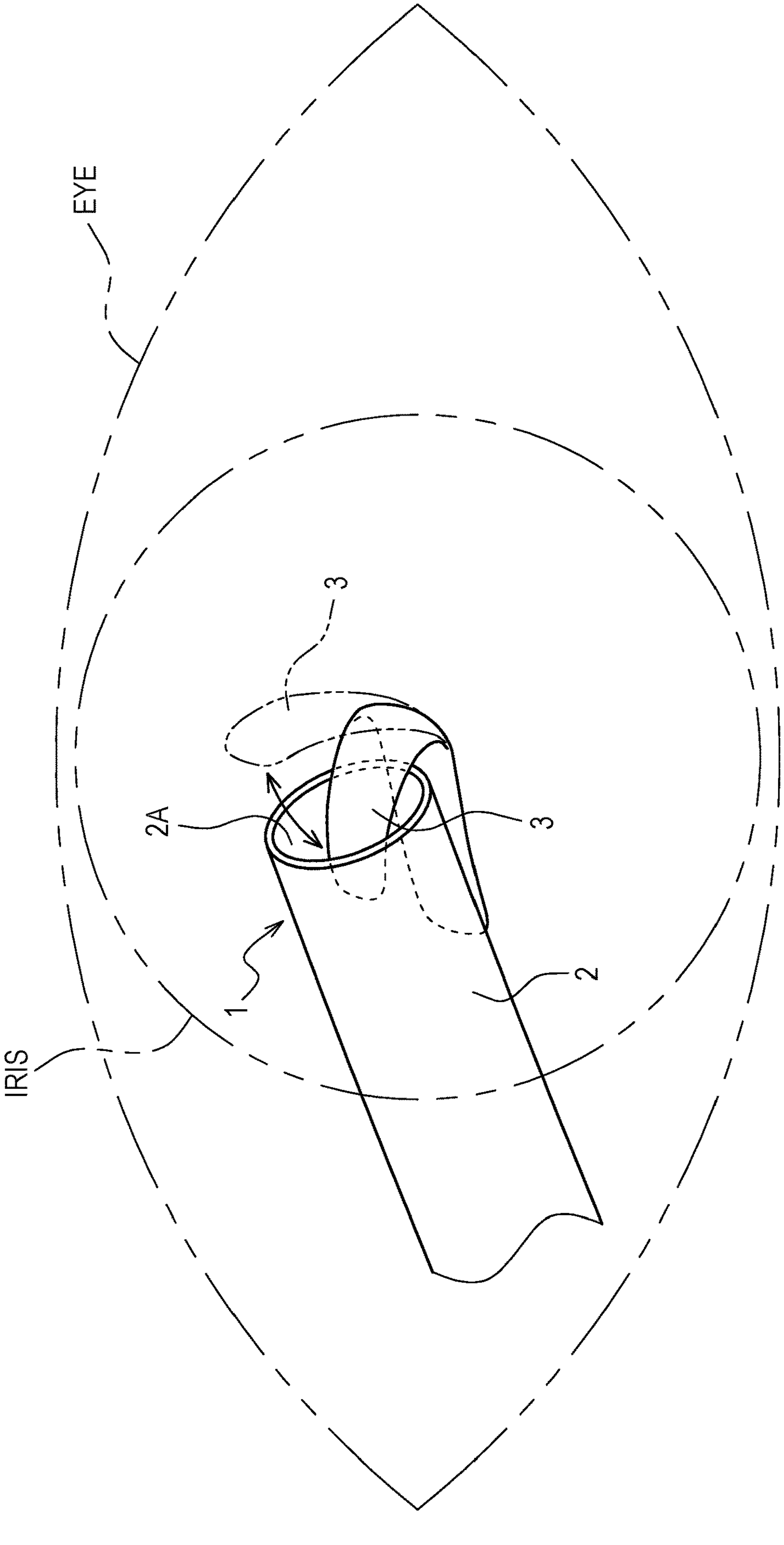
EYE
IRIS
3
3
2A
1
2

GLAUCOMA DRAINAGE TUBE

CROSS-REFERENCE TO RELATED APPLICATIONS

This application claims the benefit of Japanese Patent Application No. 2021-132238 filed on Aug. 16, 2021 with the Japan Patent Office, the entire disclosure of which is incorporated herein by reference.

BACKGROUND

The present disclosure relates to a glaucoma drainage tube for draining aqueous humor out of an eye.

As described in the U.S. Pat. No. 7,431,709, the glaucoma drainage tube is a tubing inserted into the eye, through which aqueous humor within the eye is drained.

SUMMARY

The present disclosure discloses an example of the glaucoma drainage tube that enables an ophthalmologist to evaluate a health condition of a patient's eye after a shunt surgery using the glaucoma drainage tube, and also enables a physician such as an ophthalmologist to make a clear assessment of a correlation between an exercise performed by the patient and an ocular hypotensive effect.

The glaucoma drainage tube according to the present disclosure is based on a knowledge presented in a presentation given by a medical doctor, who is the inventor of the present disclosure, at the World Glaucoma Congress (WGC) held in 2021.

The presentation was made public as a film having won the world's third prize at the Film Festival of the WGC in 2021, and the details are introduced as a paper published in Medicine (Baltimore).

The glaucoma drainage tube, based on the knowledge, for draining aqueous humor preferably comprises, for example, a canal through which aqueous humor flows, and a displacement member that is arranged at an inlet of the canal and is displaced so as to reciprocate in response to a flow of the aqueous humor flowing therein.

Such a configuration enables an ophthalmologist to evaluate the health condition of the patient's eye after the shunt surgery using the glaucoma drainage tube by observing a motion (or displacement) of the displacement member, and also enables the physician such as the ophthalmologist to make a clear assessment of the correlation between the exercise performed by the patient and the ocular hypotensive effect.

It is preferable that the displacement member is configured in a form of a cardiac valve. With such a configuration, it is possible for the physician such as the ophthalmologist to take advantage of a knowledge that a cardiac surgeon accesses a health condition of a patient from a status of the patient's cardiac valve, to make a clear assessment of the correlation between the exercise performed by the glaucoma patient and the ocular hypotensive effect.

It is preferable that the displacement member has physical properties equal to those of a fibrin membrane (a membrane or film made from a clotting component of blood). Owing to this, it is possible to obtain a displacement member having elasticity.

BRIEF DESCRIPTION OF THE DRAWINGS

An example embodiment of the present disclosure will be described hereinafter by way of example with reference to the accompanying drawing, in which:

FIG. 1 is an illustration of a glaucoma drainage tube of an embodiment.

DETAILED DESCRIPTION OF EXEMPLARY EMBODIMENTS

The following embodiment shows an example of embodiments belonging to the technical scope of the present disclosure. In other words, matters used to specify the disclosure recited in claims are not limited to specific configurations and structures shown in the following embodiment.

At least one member or part described with at least a reference numeral is provided, except where "one" or the like is omitted. That is, when there is no notice such as "one", two or more members may be provided. The glaucoma drainage tube in the present disclosure comprises an element such as a member or part described with at least a reference numeral, and a structural part shown in drawings.

<1. Configuration of Glaucoma Drainage Tube>

As shown in FIG. 1, a glaucoma drainage tube 1 of the present embodiment at least comprises a canal 2, and a displacement member 3. The canal 2 is a tubing through which aqueous humor within an eye flows. The canal 2 is implanted such that an inlet 2A of the canal 2 is placed inside an eyeball.

The displacement member 3 is a fin-like film, arranged at the inlet 2A of the canal 2. As indicated by solid lines and two-dot chain lines in FIG. 1, the displacement member 3 is displaced so as to reciprocate in response to a flow of the aqueous humor flowing therein.

The canal 2 and the displacement member 3 are made from soft resin, and may be formed from a material such as a Styrene-Isobutylene-Styrene (SIBS) block copolymer. The displacement member 3 may be a single piece formed integrally with the canal 2, or may be produced separately from and then joined to the canal 2, thereby being integrated with the canal 2.

It is preferable that the displacement member 3 is configured, for example, in a form of a cardiac valve. The displacement member 3 in the form of a cardiac valve means that the displacement member 3 has a shape and motion characteristics that mimic those of a cardiac valve. It is preferable that the displacement member 3 has physical properties equal to those of a fibrin membrane.

<2. Characteristics of Glaucoma Drainage Tube According to the Present Embodiment>

The glaucoma drainage tube 1 of the present embodiment is based on a knowledge presented in a film having won the world's third prize at the Film Festival of the World Glaucoma Congress (WGC) held in 2021.

An abridged version of the film can be viewed from the following URL:

<URL:https://www.youtube.com/watch?v=srLSBEmm4Ew>.

A paper detailing the content of the film be viewed from the following URL:

<URL::https://journals.lww.com/md-journal/Fulltext/2021/07090/Heart_rhythm_synchronized_fibrin_flap_in_a.50.aspx>

The World Glaucoma Congress (WGC) is a congress which is independent, impartial, ethical, global organization for glaucoma science and care. The core purpose of WGC is to eliminate glaucoma-related disability worldwide.

The members and decision-makers (hereinafter, they are collectively referred to as members) of the WGC are all healthcare professionals. The members of the WGC offer their time and expertise to the WGC freely, while continuing their daily, high-paced clinical and/or research work.

All the members of the WGC are world-renowned experts in the field of glaucoma. For this reason, the members' opinions are routinely sought, and their papers are regularly published and referenced. That is, contents presented in the WGC are sources of high quality, evidence-based science that contributes the progress of glaucoma medicine (referenced from: https://wga.one).

The glaucoma drainage tube 1 of the present embodiment is a tubing based on the knowledge presented in the film having won the world's third prize at the Film Festival of the WGC in 2021 and in a paper published in Medicine (Baltimore).

Specifically, the glaucoma drainage tube 1 of the present disclosure comprises, at the inlet 2A of the canal 2, the displacement member 3 having a fin-like configuration that can reciprocate in response to the flow of the aqueous humor flowing therein.

This enables an ophthalmologist to evaluate a health condition of a patient's eye after a shunt surgery using the glaucoma drainage tube 1 by observing a motion (or displacement) of the displacement member 3, and also enables a physician such as the ophthalmologist to make a clear assessment of a correlation between an exercise performed by the patient and an ocular hypotensive effect.

It is preferable that the displacement member 3 is configured in a form of a cardiac valve. With such a configuration, it is possible for the physician such as the ophthalmologist to take advantage of a knowledge that a cardiac surgeon accesses a health condition of a patient from a status of the patient's cardiac valve, to make a clear assessment of the correlation between the exercise performed by the glaucoma patient and the ocular hypotensive effect.

Specifically, as introduced in the paper and the film presented at the WGC by the inventor of the present disclosure, in observing the patient with the glaucoma drainage tube inserted, it was confirmed that the displacement member having a fin-like (flap) configuration, made out of a fibrin, made movements so as to mimic a cardiac valve when the aqueous humor flows into the canal. Thus, it is possible for the physician such as the ophthalmologist to take advantage of the knowledge that the cardiac surgeon accesses the health condition of the patient from the status of the patient's cardiac valve, to make a clear assessment of the correlation between the exercise performed by the patient and the ocular hypotensive effect.

Other Embodiments

In the above-described embodiment, the displacement member 3 and the canal 2 are integrated. However, the present disclosure is not limited to this. That is, the displacement member 3 and the canal 2 in the present disclosure may be, for example, separate components.

Furthermore, the present disclosure is only required to conform to the gist of the disclosure described in the above-described embodiments, and thus is not limited to the aforementioned embodiments. Accordingly, the present disclosure may be configured in combination of at least two of the aforementioned embodiments, or may be configured without some of the components illustrated in the drawings or described with reference numerals in the aforementioned embodiments.

What is claimed is:

1. A glaucoma drainage tube for draining aqueous humor, the glaucoma drainage tube comprising:
- a canal through which the aqueous humor flows; and
- a displacement member that is arranged at an inlet of the canal and is displaced so as to reciprocate in response to a flow of the aqueous humor flowing therein,
- the glaucoma drainage tube being arranged, in a patient's eye, in a position that allows an ophthalmologist to observe a motion of the displacement member to thereby visually recognize the flow of the aqueous humor.

2. The glaucoma drainage tube according to claim 1, wherein the displacement member has a shape imitating a cardiac valve and is configured as a reciprocable fin.

3. The glaucoma drainage tube according to claim 1, wherein the displacement member is formed of fibrin.

4. The glaucoma drainage tube according to claim 2, wherein the displacement member is formed of fibrin.

5. The glaucoma drainage tube according to claim 1, wherein the canal and the displacement member are integrally formed as a single piece.

6. The glaucoma drainage tube according to claim 1, wherein the displacement member is formed to be narrower in width than the inlet of the canal and is configured such that part of the displacement member is allowed to move in and out of the canal through the inlet of the canal.

7. A method of evaluating a health condition of an eye using a glaucoma drainage tube, the method comprising:
- arranging the glaucoma drainage tube including a displacement member in a patient's eye; and
- observing a motion of the displacement member,
- the glaucoma drainage tube being configured to drain aqueous humor, the glaucoma drainage tube including: a canal through which the aqueous humor flows; and the displacement member,
- the displacement member being arranged at an inlet of the canal and being configured to be displaced so as to reciprocate in response to a flow of the aqueous humor flowing therein.

* * * * *